United States Patent
Liu et al.

(10) Patent No.: US 10,751,670 B2
(45) Date of Patent: Aug. 25, 2020

(54) HIGH SELECTIVITY FACILITATED TRANSPORT MEMBRANE COMPRISING POLYETHERSULFONE/POLYETHYLENE OXIDE-POLYSILSESQUIOXANE BLEND MEMBRANE FOR OLEFIN/PARAFFIN SEPARATIONS

(71) Applicant: UOP LLC, Des Plaines, IL (US)

(72) Inventors: Chunqing Liu, Arlington Heights, IL (US); Nicole K. Karns, Des Plaines, IL (US); Howie Q. Tran, Skokie, IL (US); Dung Le, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 165 days.

(21) Appl. No.: 16/040,289

(22) Filed: Jul. 19, 2018

(65) Prior Publication Data

US 2019/0060841 A1    Feb. 28, 2019

Related U.S. Application Data

(60) Provisional application No. 62/549,820, filed on Aug. 24, 2017.

(51) Int. Cl.
| | |
|---|---|
| *B01D 69/14* | (2006.01) |
| *C07C 7/144* | (2006.01) |
| *B01D 67/00* | (2006.01) |
| *B01D 69/02* | (2006.01) |
| *B01D 69/12* | (2006.01) |
| *B01D 71/08* | (2006.01) |
| *B01D 53/22* | (2006.01) |
| *B01D 69/10* | (2006.01) |
| *B01D 71/70* | (2006.01) |
| *B01D 71/68* | (2006.01) |
| *B01D 71/02* | (2006.01) |
| *B01D 71/52* | (2006.01) |

(52) U.S. Cl.
CPC ......... *B01D 69/148* (2013.01); *B01D 53/228* (2013.01); *B01D 67/0013* (2013.01); *B01D 67/0079* (2013.01); *B01D 67/0088* (2013.01); *B01D 69/02* (2013.01); *B01D 69/10* (2013.01); *B01D 69/122* (2013.01); *B01D 69/142* (2013.01); *B01D 71/08* (2013.01); *C07C 7/144* (2013.01); *B01D 71/022* (2013.01); *B01D 71/52* (2013.01); *B01D 71/68* (2013.01); *B01D 71/70* (2013.01); *B01D 2256/24* (2013.01); *B01D 2257/7022* (2013.01); *B01D 2323/08* (2013.01); *B01D 2323/12* (2013.01); *B01D 2323/46* (2013.01); *B01D 2325/022* (2013.01); *B01D 2325/023* (2013.01); *B01D 2325/16* (2013.01); *B01D 2325/36* (2013.01)

(58) Field of Classification Search
CPC .. B01D 53/22; B01D 53/228; B01D 67/0013; B01D 67/0079; B01D 67/0088; B01D 69/02; B01D 69/10; B01D 69/12; B01D 69/122; B01D 69/125; B01D 69/14; B01D 69/141; B01D 69/142; B01D 71/08; B01D 71/52; B01D 71/68; B01D 71/70; B01D 2257/7022; B01D 2325/022; C07C 7/144

See application file for complete search history.

(56) References Cited

U.S. PATENT DOCUMENTS

| | | | |
|---|---|---|---|
| 3,133,132 | A | 5/1964 | Sidney et al. |
| 5,198,316 | A | 3/1993 | Wernet et al. |
| 5,256,295 | A | 10/1993 | Baker et al. |
| 5,670,051 | A | 9/1997 | Pinnau et al. |
| 6,932,589 | B2 | 8/2005 | Suzuki |
| 7,048,846 | B2 | 5/2006 | White et al. |
| 7,125,935 | B2 | 10/2006 | Andrews et al. |
| 7,361,800 | B2 | 4/2008 | Herrera et al. |
| 7,803,275 | B2 | 9/2010 | Partridge et al. |
| 8,173,323 | B2 | 5/2012 | An et al. |
| 8,337,598 | B2 | 12/2012 | Yates et al. |
| 8,366,804 | B2 | 2/2013 | Liu et al. |
| 8,561,812 | B2 | 10/2013 | Liu et al. |

(Continued)

FOREIGN PATENT DOCUMENTS

| | | |
|---|---|---|
| CN | 103402614 A | 11/2013 |
| CN | 104275094 A | 1/2015 |

(Continued)

OTHER PUBLICATIONS

Chen, "Bioinspired fabrication of composite pervaporation membranes with high permeation flux and structural stability", Journal of Membrane Science 344 (2009) 136-143.

(Continued)

*Primary Examiner* — Jason M Greene

(57) ABSTRACT

This invention provides a new high selectivity stable facilitated transport membrane comprising a polyethersulfone (PES)/polyethylene oxide-polysilsesquioxane (PEO-Si) blend support membrane, a hydrophilic polymer inside the pores on the skin layer surface of the PES/PEO-Si blend support membrane; a hydrophilic polymer coated on the skin layer surface of the PES/PEO-Si blend support membrane, and metal salts incorporated in the hydrophilic polymer coating layer and the skin layer surface pores of the PES/PEO-Si blend support membrane, and methods of making such membranes. This invention also provides a method of using the high selectivity stable facilitated transport membrane comprising PES/PEO-Si blend support membrane for olefin/paraffin separations such as propylene/propane and ethylene/ethane separations.

17 Claims, No Drawings

(56) References Cited

U.S. PATENT DOCUMENTS

| | | |
|---|---|---|
| 8,574,785 B2 | 11/2013 | Kim et al. |
| 8,829,059 B2 | 9/2014 | Wynn et al. |
| 8,912,288 B2 | 12/2014 | Liu et al. |
| 9,017,451 B2 | 4/2015 | Wynn et al. |
| 9,126,152 B2 | 9/2015 | Liu et al. |
| 9,126,154 B2 | 9/2015 | Liu et al. |
| 9,126,156 B2 | 9/2015 | Liu et al. |
| 9,211,508 B2 | 12/2015 | Liu et al. |
| 9,216,390 B2 | 12/2015 | Ho et al. |
| 9,751,050 B2 | 9/2017 | Zhou et al. |
| 10,258,929 B2 | 4/2019 | Liu et al. |
| 2004/0154980 A1 | 8/2004 | Kim et al. |
| 2004/0215045 A1* | 10/2004 | Herrera ............... B01D 53/228 585/818 |
| 2006/0000778 A1 | 1/2006 | Childs et al. |
| 2007/0190385 A1 | 8/2007 | Lee et al. |
| 2008/0063917 A1 | 3/2008 | Yamashita et al. |
| 2008/0268314 A1 | 10/2008 | Han et al. |
| 2009/0277837 A1 | 11/2009 | Liu et al. |
| 2010/0018926 A1 | 1/2010 | Liu et al. |
| 2010/0147148 A1 | 6/2010 | Rabiei |
| 2011/0094960 A1 | 4/2011 | Zhou et al. |
| 2012/0031833 A1 | 2/2012 | Ho et al. |
| 2012/0285881 A1 | 11/2012 | Jikihara et al. |
| 2013/0255483 A1 | 10/2013 | Sanders et al. |
| 2013/0299428 A1 | 11/2013 | Bikel et al. |
| 2013/0233791 A1 | 12/2013 | Koo et al. |
| 2014/0137734 A1 | 5/2014 | Liu et al. |
| 2014/0290478 A1 | 10/2014 | Liu et al. |
| 2015/0025293 A1 | 1/2015 | Feiring et al. |
| 2015/0053079 A1 | 2/2015 | Koros et al. |
| 2015/0068978 A1 | 3/2015 | Lando et al. |
| 2015/0098872 A1 | 4/2015 | Kelly et al. |
| 2016/0107127 A1* | 4/2016 | Lee ...................... B01D 69/125 96/4 |
| 2016/0177035 A1 | 6/2016 | Liu et al. |
| 2016/0325229 A1 | 11/2016 | Zhou et al. |
| 2017/0291143 A1 | 10/2017 | Zhou et al. |
| 2017/0354918 A1 | 12/2017 | Liu et al. |
| 2018/0001277 A1 | 1/2018 | Liu et al. |
| 2018/0154311 A1 | 6/2018 | Zhou et al. |
| 2018/0333675 A1 | 11/2018 | Liu et al. |
| 2018/0345230 A1 | 12/2018 | Karns et al. |
| 2019/0060841 A1 | 2/2019 | Liu et al. |

FOREIGN PATENT DOCUMENTS

| | | |
|---|---|---|
| EP | 458598 A2 | 11/1991 |
| EP | 1375459 A1 | 1/2004 |
| EP | 2545985 A1 | 1/2013 |
| EP | 2764908 A1 | 8/2014 |
| WO | 2009002747 A2 | 12/2008 |

OTHER PUBLICATIONS

Ma, "High-flux thin-film nanofibrous composite ultrafiltration membranes containing cellulose barrier layer", J. Mater. Chem., 2010, 20, 4692-4704 (2010).

Wanichapichart, Characteristics of polyethersulfone/chitosan composite membranes:, Biophysics Unit, Membrane Science and Technology Research Center, Faculty of Science, Prince of Songkia University, Had Yai, Songkhla, Thailand 90112.

Riley, "Thin-Film Composite Membrane for Single-Stage Seawater Desalination by Reverse Osmosis", Applied Polymer Symposium No. 22, pp. 255-267 (1973).

Hess et al., Prpene/prpane separation with copolyimide membranes containing silver ions, Journal of Membrane Science, vol. 275, issue 1-2, Apr. 20, 2006, pp. 52-60.

PCT Search Report dated Sep. 14, 2017 for PCT Application No. PCT/US2017/038294.

Kang, "Novel Application of Partially Positively Charged Silver Nanoparticles for Facilitated Transport in Olefin/Paraffin Separation Membranes", Chem. Mater. 2008, 20, 1308-1311.

PCT Search Report dated Oct. 5, 2017 for PCT Appl. No. PCT/US2017/038307.

PCT Search Report dated Aug. 30, 2018 for PCT Appl. No. PCT/US2018/032251.

PCT Search Report dated Sep. 14, 2017 for PCT Appl. No. PCT/US2017/036265.

Kudinov, "Separation Characteristics of an Ejector Membrane-Sorption Hybrid System", Theoretical Foundations of Chemical Engineering, 2014, vol. 48, No. 6, 832-836, Pleiades Publishing, Ltd., 2014.

PCT Search Report dated Aug. 30, 2018 for PCT Appl. No. PCT/US2018/035004.

PCT Search Report dated Nov. 29, 2018 for PCT Appl. No. PCT/US2018/047547.

* cited by examiner

HIGH SELECTIVITY FACILITATED TRANSPORT MEMBRANE COMPRISING POLYETHERSULFONE/POLYETHYLENE OXIDE-POLYSILSESQUIOXANE BLEND MEMBRANE FOR OLEFIN/PARAFFIN SEPARATIONS

CROSS-REFERENCE TO RELATED APPLICATION

This application claims priority from Provisional Application No. 62/549,820 filed Aug. 24, 2017, the contents of which cited application are hereby incorporated by reference in its entirety.

BACKGROUND OF THE INVENTION

Over 170 Separex™ membrane systems have been installed in the world for gas separation applications such as for the removal of acid gases from natural gas, in enhanced oil recovery, and hydrogen purification. Two new Separex™ membranes (Flux+ and Select) have been commercialized recently by Honeywell UOP, Des Plaines, Ill. for carbon dioxide removal from natural gas. These Separex™ spiral wound membrane systems currently hold the membrane market leadership for natural gas upgrading. These membranes, however, do not have outstanding performance for olefin/paraffin separations. Development of new stable and very high selectivity membranes is critical for the future success of membranes for olefin/paraffin separation applications such as propylene/propane and ethylene/ethane separations.

Light olefins, such as propylene and ethylene, are produced as co-products from a variety of feedstocks in many different processes in the chemical, petrochemical, and petroleum refining industries. Various petrochemical streams contain olefins and other saturated hydrocarbons. Typically, these streams are from stream cracking units (ethylene production), catalytic cracking units (motor gasoline production), or the dehydrogenation of paraffins.

Currently, the separation of olefin and paraffin components is performed by cryogenic distillation, which is expensive and energy intensive due to the low relative volatilities of the components. Large capital expenses and energy costs have created incentives for extensive research in this area of separations, and low energy-intensive membrane separations have been considered as an attractive alternative.

In principle, membrane-based technologies have the advantage of both low capital cost and high-energy efficiency compared to conventional separation methods for olefin/paraffin separations, such as propylene/propane and ethylene/ethane separations. Four main types of membranes have been reported for olefin/paraffin separations. These are facilitated transport membranes, polymer membranes, mixed matrix membranes, and inorganic membranes. Facilitated transport membranes, or ion exchange membranes, which sometimes use silver ions as a complexing agent, have very high olefin/paraffin separation selectivity. However, poor chemical stability, due to carrier poisoning or loss, high cost, and low flux, currently limit practical applications of facilitated transport membranes.

Separation of olefins from paraffins via conventional polymer membranes has not been commercially successful due to inadequate selectivities and permeabilities of the polymer membrane materials, as well as due to plasticization issues. Polymers that are more permeable are generally less selective than are less permeable polymers. A general trade-off has existed between permeability and selectivity (the so-called "polymer upper bound limit") for all kinds of separations, including olefin/paraffin separations. In recent years, substantial research effort has been directed to overcoming the limits imposed by this upper bound. Various polymers and techniques have been used, but without much success in terms of improving the membrane selectivity.

More efforts have been undertaken to develop metal ion incorporated, high olefin/paraffin selectivity facilitated transport membranes. The high selectivity for olefin/paraffin separations is achieved by the incorporation of metal ions such as silver (I) or copper (I) cations into the solid nonporous polymer matrix layer on top of the highly porous membrane support layer (so-called "fixed site carrier facilitated transport membrane") or directly into the pores of the highly porous support membrane (so-called "supported liquid facilitated transport membrane") that results in the formation of a reversible metal cation complex with the pi bond of olefins, whereas no interaction occurs between the metal cations and the paraffins. Addition of water, plasticizer, or humidification of the olefin/paraffin feed streams to either the fixed site carrier facilitated transport membranes or the supported liquid facilitated transport membranes is usually required to obtain reasonable olefin permeances and high olefin/paraffin selectivities. The performance of fixed site carrier facilitated transport membranes is much more stable than that of the supported liquid facilitated transport membranes and the fixed site carrier facilitated transport membranes are less sensitive to the loss of metal cation carriers than the supported liquid facilitated transport membranes.

Pinnau et al. disclosed a solid polymer electrolyte fixed site carrier facilitated transport membrane comprising silver tetrafluoroborate incorporated poly(ethylene oxide), see U.S. Pat. No. 5,670,051. Herrera et al. disclosed a process for the separation of olefin/paraffin mixtures using a silver cation-chelated chitosan fixed site carrier facilitated transport membrane, see U.S. Pat. No. 7,361,800. Herrera et al. also disclosed the coating of a layer of chitosan on the surface of a microporous support membrane, where the support membrane is made from polyesters, polyamides, polyimides, polyvinylidene fluoride, polyacrylonitrile, polysulfones or polycarbonates.

Feiring et al. disclosed a new facilitated transport membrane comprising silver (I) cation exchanged fluorinated copolymer synthesized from a perfluorinated cyclic or cyclizable monomer and a strong acid highly fluorinated vinylether compound, see US 2015/0025293.

The composite facilitated transport membranes disclosed in the literature use an ultrafiltration or microfiltration membrane as the support membrane. However, the use of a relatively hydrophilic, nanoporous polymeric membrane such as a polyethersulfone membrane as the support membrane for the preparation of fixed site carrier facilitated transport membranes for olefin/paraffin separations has not been reported in the literature. In particular, the use of a relatively hydrophilic, very small pore, nanoporous support membranes with an average pore diameter of less than 10 nm on the membrane skin layer surface for the preparation of fixed site carrier facilitated transport membranes has not been disclosed in the literature.

Development of new stable, high permeance, and high selectivity facilitated transport membranes is still required for the use of membranes for olefin/paraffin separations such as propylene/propane and ethylene/ethane separations.

SUMMARY OF THE INVENTION

The invention provides a membrane comprising an asymmetric polyethersulfone/polyethylene oxide-polysilsesquioxane blend support membrane comprising a polyethylene oxide-polysilsesquioxane polymer and a polyethersulfone polymer; a hydrophilic polymer inside the pores on the skin layer surface of the polyethersulfone/polyethylene oxide-polysilsesquioxane blend support membrane; a hydrophilic polymer coated on the skin layer surface of the polyethersulfone/polyethylene oxide-polysilsesquioxane blend support membrane, and metal salts incorporated in the hydrophilic polymer coating layer and the skin layer surface pores of the polyethersulfone/polyethylene oxide-polysilsesquioxane blend support membrane.

An embodiment of the invention involves a method of making a facilitated transport membrane comprising the steps of: (a) preparing a polyethersulfone/polyethylene oxide-polysilsesquioxane blend support membrane using a homogeneous solution comprising polyethersulfone, N,N'-bis-[(3-triethoxysilylpropyl)aminocarbonyl]-polyethylene oxide monomer, a mixture of a solvent, one or more non-solvents, and additives; (b) incorporating a hydrophilic polymer inside pores on the skin layer surface of said polyethersulfone/polyethylene oxide-polysilsesquioxane blend support membrane; (c) coating a thin, nonporous, hydrophilic polymer layer on the skin layer surface of the polyethersulfone/polyethylene oxide-polysilsesquioxane blend support membrane; and (d) impregnating the surface of the hydrophilic polymer-coated polyethersulfone/polyethylene oxide-polysilsesquioxane blend support membrane with an aqueous solution of a metal salt.

The invention also provides a process to treat a gaseous feed stream comprising from 99 to 1 mole % of one or more C2-C8 olefins and from 1 to 99 mole % of one or more C1-C8 paraffins or other gases such as nitrogen wherein said process comprises passing the gaseous feed stream to a feed side of a facilitated transport membrane comprising a polyethersulfone/polyethylene oxide-polysilsesquioxane blend support membrane, a hydrophilic polymer inside pores on the skin layer surface of said support membrane, a thin, nonporous, hydrophilic polymer layer coated on the skin layer surface of said support membrane, and metal salts incorporated in said hydrophilic polymer layer coated on the surface of said support membrane and the skin layer surface pores of said support membrane, wherein not less than 80 mole % of the olefins in said feed stream pass through said facilitated transport membrane to become a permeate stream and then recovering the permeate stream comprising not less than 90 mole % of olefin and not more than 10 mole % of paraffin or other gases.

DESCRIPTION OF THE INVENTION

This invention provides a new high selectivity stable facilitated transport membrane comprising an asymmetric polyethersulfone (PES)/polyethylene oxide-polysilsesquioxane (PEO-Si) blend support membrane, a hydrophilic polymer inside the pores on the skin layer surface of the PES/PEO-Si blend support membrane; a hydrophilic polymer coated on the skin layer surface of the PES/PEO-Si blend support membrane, and metal salts incorporated in the hydrophilic polymer coating layer and the skin layer surface pores of the PES/PEO-Si blend support membrane and methods of making such membranes. This invention also provides a method of using the high selectivity stable facilitated transport membrane comprising PES/PEO-Si blend support membrane for olefin/paraffin separations such as propylene/propane and ethylene/ethane separations.

The polyethersulfone (PES)/polyethylene oxide-polysilsesquioxane (PEO-Si) blend support membrane described in the present invention comprises polyethersulfone (PES) and polyethylene oxide-polysilsesquioxane (PEO-Si) polymer and the polyethylene oxide polymer chain segment is much more hydrophilic than PES polymer. Therefore, the PES/PEO-Si blend support membrane is more hydrophilic than the PES only membrane. The improved hydrophilicity of the PES/PEO-Si blend support membrane significantly improved the performance stability of the facilitated transport membrane described in the present invention comprising the PES/PEO-Si blend support membrane, a hydrophilic polymer inside the pores on the skin layer surface of the PES/PEO-Si blend support membrane, a hydrophilic polymer coated on the skin layer surface of the PES/PEO-Si blend support membrane, and metal salts incorporated in the hydrophilic polymer layer coated on surface of the PES/PEO-Si blend support membrane and the skin layer surface pores of the PES/PEO-Si blend support membrane. The PES/PEO-Si blend support membrane in the facilitated transport membrane described in the present invention improves the solavation and interaction of the metal salts such as silver nitrate with the hydrophilic polyethylene oxide (PEO) polymer chains. The PEO polymer chains were stabilized in the support membrane via covalent bonding between PEO and polysilsesquioxane polymer chains.

The polyethylene oxide-polysilsesquioxane (PEO-Si) polymer in the polyethersulfone (PES)/polyethylene oxide-polysilsesquioxane (PEO-Si) blend support membrane described in the present invention was insoluble in water and was prepared from N,N'-bis-[(3-triethoxysilylpropyl)aminocarbonyl]-polyethylene oxide monomer. The N,N'-bis-[(3-triethoxysilylpropyl)aminocarbonyl]-polyethylene oxide monomer was hydrolyzed and polymerized during the membrane casting dope preparation and membrane fabrication process.

The polyethersulfone (PES)/polyethylene oxide-polysilsesquioxane (PEO-Si) blend support membrane described in the present invention has an average pore diameter of less than 10 nm on the membrane skin layer surface. The PES/PEO-Si blend support membrane is an asymmetric integrally skinned membrane with either flat sheet (spiral wound) or hollow fiber geometry.

The hydrophilic polymer inside the pores on the skin layer surface of the PES/PEO-Si blend support membrane can be selected from, but is not limited to, a group of hydrophilic polymers containing chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof.

The thin, nonporous, hydrophilic polymer layer coated on the skin layer surface of PES/PEO-Si blend support membrane for the preparation of the facilitated transport membrane comprises a hydrophilic polymer selected from, but is not limited to, a group of hydrophilic polymers containing chitosan, sodium carboxylmethyl-chitosan, carboxylmethyl-chitosan, hyaluronic acid, sodium hyaluronate, carbopol, polycarbophil calcium, poly(acrylic acid) (PAA), poly (methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof. The hydrophilic polymer in the thin, nonporous, hydrophilic polymer layer coated on the skin layer surface of PES/PEG-Si blend support membrane and the hydrophilic polymer inside the pores on the skin layer surface of PES/PEO-Si blend support membrane can be selected from the same hydrophilic polymer or different hydrophilic polymers. Preferably, the hydrophilic polymer in the thin, nonporous, hydrophilic polymer layer coated on the skin layer surface of PES/PEO-Si blend support membrane and the hydrophilic polymer inside the pores on the skin layer surface of the PES/PEO-Si blend support membrane are selected from different hydrophilic polymers. As an example in an embodiment of the invention, the hydrophilic polymer in the thin, nonporous, hydrophilic polymer layer coated on the skin layer surface of PES/PEO-Si blend support membrane is chitosan and the hydrophilic polymer inside the pores on the skin layer surface of PES/PEO-Si blend support membrane is sodium alginate or sodium hyaluronate.

The metal salts incorporated in the hydrophilic polymer layer coated on the skin layer surface of the PES/PEO-Si blend support membrane and the skin layer surface pores of the PES/PEO-Si blend support membrane for the preparation of the facilitated transport membrane are preferred to be selected from silver salts or copper salts, such as silver(I) nitrate or copper(I) chloride.

The metal cations such as silver cations on the metal salts incorporated in the hydrophilic polymer layer coated on the skin layer surface of the PES/PEO-Si blend support membrane and the skin layer surface pores of the PES/PEO-Si blend support membrane of the facilitated transport membrane in the current invention form reversible metal cation complexes with the pi bonds of olefins, while no interactions occur between the metal cations and the paraffins or other gases such as nitrogen in the facilitated transport membrane. Therefore, the facilitated transport membranes comprising the PES/PEO-Si blend support membrane, a hydrophilic polymer inside the pores on the skin layer surface of said support membrane, a thin, nonporous, hydrophilic polymer layer coated on the skin layer surface of said support membrane, and metal salts incorporated in the hydrophilic polymer layer coated on the skin layer surface of the support membrane and the skin layer surface pores of the PES/PEO-Si blend support membrane can provide both high selectivity and high permeance for olefin/paraffin separations.

Olefin/paraffin permeation experimental results demonstrated that the facilitated transport membrane prepared from the PES/PEO-Si blend support membrane described in the current invention showed super high performance stability, high olefin/paraffin selectivity, and good olefin permeance for olefin/paraffin separations. The present invention discloses a method of making the new facilitated transport membranes comprising PES/PEO-Si blend porous support membrane, a hydrophilic polymer inside the pores on the skin layer surface of the PES/PEO-Si blend porous support membrane, a thin, nonporous, hydrophilic polymer layer coated on the skin layer surface of the PES/PEO-Si blend support membrane, and metal salts incorporated in the hydrophilic polymer layer coated on the skin layer surface of the PES/PEO-Si blend support membrane and the skin layer surface pores of the PES/PEO-Si blend support membrane. The method of making these membranes comprises of first the preparation of a PES/PEO-Si blend polymer casting or spinning solution by dissolving PES and N,N'-bis-[(3-triethoxysilylpropyl)aminocarbonyl]-polyethylene oxide monomer in a mixture of a solvent such as a mixture of N-methyl-2-pyrrolidone (NMP) and 1,3-dioxolane, one or more non-solvents such as an alcohol or a hydrocarbon, and additives such as a mixture of glycerol, lactic acid and water to form a homogeneous solution. The N,N'-bis-[(3-triethoxysilylpropyl)aminocarbonyl]-polyethylene oxide monomer will hydrolyze and polymerize in the presence of a lactic acid catalyst to form a polyethylene oxide-polysilsesquioxane polymer (PEO-Si) during this process; The next step is preparation of a PES/PEO-Si blend support membrane comprising hydrophilic polymers inside the pores on the skin layer surface of said support membrane via a phase inversion membrane casting or spinning fabrication process, and the incorporation of the hydrophilic polymers into the pores on the skin layer surface of the support membrane is accomplished by the nipping of an aqueous solution of a hydrophilic polymer with a polymer concentration in a range of 0.02 wt % to 5 wt % at the end of the membrane casting or spinning fabrication process or via the addition of the hydrophilic polymer to the gelation water tank during the membrane casting or spinning fabrication process. This step is followed by coating a thin, nonporous, hydrophilic polymer layer on the skin layer surface of the PES/PEO-Si blend support membrane comprising hydrophilic polymers inside the pores on the skin layer surface of the support membrane via any coating method such as dip-coating or meniscus coating method using an aqueous solution of the hydrophilic polymer with a concentration in a range of 0.2 wt % to 10 wt %. The new facilitated transport membrane is then prepared by soaking the thin, nonporous, hydrophilic polymer layer coated on the skin layer surface of the PES/PEO-Si blend support membrane comprising hydrophilic polymers inside the pores on the skin layer surface of the support membrane in an aqueous solution of a metal salt such as silver nitrate ($AgNO_3$) with a concentration in a range of 0.2M to 10M for a predetermined time in a range from 1 min to 48 h.

The present invention provides a process to treat a gaseous feed stream comprising from 99 to 1 mole % of one or more C2-C8 olefins and from 1 to 99 mole % of one or more C1-C8 paraffins or other gases such as nitrogen. The process comprises passing the gaseous feed stream to a feed side of a facilitated transport membrane comprising a PES/PEO-Si blend support membrane, a hydrophilic polymer inside the pores on the skin layer surface of said support membrane, a thin, nonporous, hydrophilic polymer layer coated on the skin layer surface of said support membrane, and metal salts incorporated in said hydrophilic polymer layer coated on the skin layer surface of said support membrane and the skin layer surface pores of the PES/PEO-Si blend support membrane, so that not less than 80 mole % of the olefins in said feed stream pass through said facilitated transport membrane and recovering a permeate stream comprising not less than 90 mole % of olefin and not more than 10 mole % of paraffin or other gases such as nitrogen.

EXAMPLES

The following examples are provided to illustrate one or more preferred embodiments of the invention, but are not limited embodiments thereof. Numerous variations can be made to the following examples that lie within the scope of the invention.

Example 1

PES/PEG-Si Blend Porous Support Membrane

A hydrophilic PES/PEG-Si blend porous asymmetric integrally-skinned support membrane was prepared via a phase-inversion process. A membrane casting dope comprising, by approximate weight percentages, polyethersulfone 18-25%, N,N'-bis-[(3-triethoxysilylpropyl)aminocarbonyl]-polyethylene oxide 3-10%, N-methyl pyrrolidone 60-65%, 1,3-dioxolane 10-15%, glycerol 1-10%, lactic acid 0.5-4%, water 0-4%, and n-decane 0.5-2% was cast on a nylon or polyester fabric then gelled by immersion in a 1° C. water bath for about 10 minutes, and then annealed in a hot water bath at 85° C. for about 5 minutes. The N,N'-bis-[(3-triethoxysilylpropyl)aminocarbonyl]-polyethylene oxide monomer will hydrolyze and polymerize in the presence of a lactic acid catalyst to form a polyethylene oxide-polysilsesquioxane polymer (PEO-Si) during this process. A dilute aqueous solution of sodium alginate or chitosan was applied via a nipping method onto the skin layer surface of the wet, hydrophilic, porous, asymmetric PES/PEG-Si blend support membrane. The wet membrane comprising sodium alginate or chitosan within the pores on the membrane skin layer surface was used directly for the preparation of new facilitated transport membranes. The dried asymmetric PES/PEG-Si blend support membrane has an average pore diameter of 1.9 nm on the skin layer surface.

Example 2

Ag+-Chitosan/PES/PEG-Si Thin Film Composite (TFC) Facilitated Transport Membrane The freshly prepared wet hydrophilic PES/PEG-Si blend porous asymmetric integrally-skinned support membrane comprising sodium alginate within the pores on the membrane skin layer surface prepared in Example 1 was coated with a solution of chitosan dissolved in a dilute, aqueous acetic acid solution and then dried at 50° C. to form a thin, nonporous, chitosan layer on the skin layer surface of the membrane. The membrane was then treated with a basic sodium hydroxide solution, washed with water. The thin, nonporous, hydrophilic polymer layer coated on the skin layer surface of the PES/PEO-Si blend support membrane was then impregnated with a silver nitrate aqueous solution (3M in $H_2O$) for 15 h to form the Ag+-Chitosan/PES/PEG-Si TFC facilitated transport membrane.

Comparative Example 1

Ag+-Chitosan/PES Thin Film Composite Facilitated Transport Membrane

A porous, asymmetric polyethersulfone support membrane was prepared via the phase-inversion process. A membrane casting dope comprising, by approximate weight percentages, polyethersulfone 18-25%, N-methyl pyrrolidone 60-65%, 1,3-dioxolane 10-15%, glycerol 1-10% and n-decane 0.5-2% was cast on a nylon fabric then gelled by immersion in a 1° C. water bath for about 10 minutes, and then annealed in a hot water bath at 85° C. for about 5 minutes. A dilute aqueous solution of sodium alginate was applied via a nipping method onto the surface of the wet porous, asymmetric polyethersulfone support membrane. The wet membrane comprising sodium alginate within the pores on the membrane skin layer surface was coated with a solution of chitosan dissolved in a dilute, aqueous acetic acid solution and then dried at 50° C. to form a thin, nonporous, chitosan layer on the surface of the membrane. The membrane was then treated with a basic sodium hydroxide solution, washed with water to form the polyethersulfone support membrane comprising alginic acid within the pores on the membrane skin layer surface and a thin, nonporous, chitosan layer on the surface of the membrane. The surface of the membrane was then impregnated with a silver nitrate aqueous solution (3M in $H_2O$) to form the Ag+-Chitosan/PES TFC facilitated transport membrane.

Comparative Example 2

Ag+-Chitosan/PES/PEG-Si—OH Thin Film Composite Facilitated Transport Membrane

A hydrophilic PES/PEG-Si—OH blend porous asymmetric integrally-skinned support membrane was prepared via a phase-inversion process. A membrane casting dope comprising, by approximate weight percentages, polyethersulfone 18-25%, N,N'-bis-[(3-triethoxysilylpropyl)aminocarbonyl]-polyethylene oxide 3-10%, N-methyl pyrrolidone 60-65%, 1,3-dioxolane 10-15%, glycerol 1-10%, water 0-4%, and n-decane 0.5-2% was cast on a nylon or polyester fabric then gelled by immersion in a 1° C. water bath for about 10 minutes, and then annealed in a hot water bath at 85° C. for about 5 minutes. The N,N'-bis-[(3-triethoxysilylpropyl)aminocarbonyl]-polyethylene oxide monomer will hydrolyze without polymerization in the absence of a lactic acid catalyst during this process. A dilute aqueous solution of sodium alginate or chitosan was applied via a nipping method onto the skin layer surface of the wet, hydrophilic, porous, asymmetric PES/PEG-Si—OH blend support membrane. The wet membrane comprising sodium alginate or chitosan within the pores on the membrane skin layer surface was used directly for the preparation of the facilitated transport membranes. The dried asymmetric PES/PEG-Si—OH blend support membrane has an average pore diameter of 2.7 nm on the skin layer surface. The wet membrane comprising sodium alginate within the pores on the membrane skin layer surface was coated with a solution of chitosan dissolved in a dilute, aqueous acetic acid solution and then dried at 50° C. to form a thin, nonporous, chitosan layer on the surface of the membrane. The membrane was then treated with a basic sodium hydroxide solution, washed with water to form the PES/PEG-Si—OH blend support membrane comprising alginic acid within the pores on the membrane skin layer surface and a thin, nonporous, chitosan layer on the surface of the membrane. The surface of the membrane was then impregnated with a silver nitrate aqueous solution (3M in $H_2O$) to form the Ag+-Chitosan/PES/PEG-Si—OH TFC facilitated transport membrane.

Example 3

Propylene/Propane Separation Performance of Ag+-Chitosan/PES/PEG-Si, Ag+-Chitosan/PES/PEG-Si—OH, and Ag+-Chitosan/PES Thin Film Composite Facilitated Transport Membranes The wet facilitated transport membranes including Ag+-Chitosan/PES/PEG-Si prepared in Example 2, Ag+-Chitosan/PES prepared in Comparative Example 1, and Ag+-Chitosan/PES/PEG-Si—OH prepared in Comparative Example 2 were tested with a humidified (relative humidity 80-100%) propylene/propane ($C_3$_/$C_3$) gas mixture (70% $C_3$_/30% $C_3$) at 791 kPa (100 psig) and 50° C. respectively. Their results are shown in TABLE 1. Ag+-Chitosan/PES/PEG-Si TFC facilitated transport membrane showed a propylene permeance of 75.6 GPU and a propylene/propane selectivity of >1000 corresponding to a permeate stream with a propylene purity of >99.9% after 2 h of testing. The membrane also showed very stable permeance and selectivity after 21.5 h of continuous testing as shown in TABLE 1.

The results in TABLE 1 show that the Ag+-Chitosan/PES/PEG-Si TFC facilitated transport membrane has much more stable propylene permeance than the Ag+-Chitosan/PES and Ag+-Chitosan/PES/PEG-Si—OH TFC facilitated transport membranes, suggesting that the water insoluble hydrophilic PEG-Si polymer in the present new facilitated transport membrane improved the membrane performance stability.

TABLE 1

Propylene/propane permeation test results of the Ag+-Chitosan/PES, Ag+-Chitosan/PES/PEG-Si—OH, and Ag+-Chitosan/PES/PEG-Si TFC facilitated transport membranes

| Membrane | Testing time (h) | $P_{C3=}/L$ (GPU) | $\alpha_{C3=/C3}$ |
|---|---|---|---|
| Ag+-Chitosan/PES/PEG-Si—OH TFC [a] | 1 | 6.15 [a] | 368 |
|  | 3 | 3.70 [a] | 207 |
| Ag+-Chitosan/PES TFC [a] | 1 | 4.77 [a] | >1000 |
|  | 3 | 2.23 [b] | >1000 |
|  | 17.5 | 2.08 [b] | >1000 |
|  | 20.2 | 3.84 [a] | >1000 |
| Ag+-Chitosan/PES/PEG-Si TFC | 1 | 4.40 [a] | >1000 |
|  | 2 | 4.62 [a] | >1000 |
|  | 3 | 4.62 [a] | 1000 |
|  | 5 | 2.68 [b] | >1000 |
|  | 18 | 2.62 [b] | >1000 |
|  | 19 | 2.64 [b] | >1000 |
|  | 21.5 | 4.60 [b] | >1000 |

Tested at 50° C., 791 kPa (100 psig) propylene/propane (70%/30%) mixed vapor feed pressure; feed stream was bubbled through water at 50° C.; retentate flow rate was set at [a] 708 scc/min; [b] 200 scc/min; 1 GPU= $10^{-6}$ cm$^3$ (STP)/cm$^2$ s (cm Hg).

Specific Embodiments

While the following is described in conjunction with specific embodiments, it will be understood that this description is intended to illustrate and not limit the scope of the preceding description and the appended claims.

A first embodiment of the invention is a membrane comprising a polyethersulfone/polyethylene oxide-polysilsesquioxane blend support membrane comprising a polyethylene oxide-polysilsesquioxane polymer and a polyethersulfone polymer; a hydrophilic polymer inside the pores on the skin layer surface of the polyethersulfone/polyethylene oxide-polysilsesquioxane blend support membrane; a hydrophilic polymer coated on the skin layer surface of the polyethersulfone/polyethylene oxide-polysilsesquioxane blend support membrane, and metal salts incorporated in the hydrophilic polymer coating layer and the the skin layer surface pores of the polyethersulfone/polyethylene oxide-polysilsesquioxane blend support membrane. An embodiment of the invention is one, any or all of prior embodiments in this paragraph up through the first embodiment in this paragraph wherein the polyethersulfone/polyethylene oxide-polysilsesquioxane blend support membrane comprises pores with an average pore diameter of less than 10 nm on the skin layer surface of the blend support membrane. An embodiment of the invention is one, any or all of prior embodiments in this paragraph up through the first embodiment in this paragraph wherein the blend support membrane is an asymmetric integrally skinned membrane with either a flat sheet or hollow fiber geometry. An embodiment of the invention is one, any or all of prior embodiments in this paragraph up through the first embodiment in this paragraph wherein the hydrophilic polymer inside the pores on the skin layer surface of the polyethersulfone/polyethylene oxide-polysilsesquioxane blend support membrane is selected from the group consisting of chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof. An embodiment of the invention is one, any or all of prior embodiments in this paragraph up through the first embodiment in this paragraph wherein the hydrophilic polymer in the thin, nonporous, hydrophilic polymer layer coated on the skin layer surface of the polyethersulfone/polyethylene oxide-polysilsesquioxane support membrane and the hydrophilic polymer inside the pores on the skin layer surface of the polyethersulfone/polyethylene oxide-polysilsesquioxane blend support membrane is selected from the same hydrophilic polymer or different hydrophilic polymers. An embodiment of the invention is one, any or all of prior embodiments in this paragraph up through the first embodiment in this paragraph wherein the hydrophilic polymer in the thin, nonporous, hydrophilic polymer layer coated on the skin layer surface of the polyethersulfone/polyethylene oxide-polysilsesquioxane blend support membrane is chitosan and the hydrophilic polymer inside the pores on the skin layer surface of the polyethersulfone/polyethylene oxide-polysilsesquioxane blend support membrane is sodium alginate or sodium hyaluronate. An embodiment of the invention is one, any or all of prior embodiments in this paragraph up through the first embodiment in this paragraph wherein the metal salts are selected from the group consisting of silver salts and copper salts.

A second embodiment of the invention is a method of making a facilitated transport membrane comprising (a) preparing a polyethersulfone/polyethylene oxide-polysilsesquioxane blend support membrane using a homogeneous solution comprising polyethersulfone, N,N'-bis-[(3-triethoxysilylpropyl)aminocarbonyl]-polyethylene oxide monomer, a mixture of a solvent, one or more non-solvents, and additives; (b) incorporating a hydrophilic polymer inside pores on the skin layer surface of the polyethersulfone/polyethylene oxide-polysilsesquioxane blend support membrane; (c) coating a thin, nonporous, hydrophilic polymer layer on the skin layer surface of the polyethersulfone/polyethylene oxide-polysilsesquioxane blend support membrane; and (d) impregnating the surface of the hydrophilic polymer-coated polyethersulfone/polyethylene oxide-polysilsesquioxane blend support membrane with an aqueous solution of a metal salt. An embodiment of the invention is one, any or all of prior embodiments in this paragraph up through the second embodiment in this paragraph wherein the hydrophilic polymer is selected from the group consisting of chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof. An embodiment of the invention is one, any or all of prior embodiments in this paragraph up through the second embodiment in this paragraph wherein the N,N'-bis-[(3-triethoxysilylpropyl)aminocarbonyl]-polyethylene oxide monomer will hydrolyze and polymerize in the presence of a lactic acid catalyst to form the polyethylene oxide-polysilsesquioxane polymer.

A third embodiment of the invention is a process to treat a gaseous feed stream comprising from 99 to 1 mole % of one or more C2-C8 olefins and from 1 to 99 mole % of one or more C1-C8 paraffins or other gases such as nitrogen wherein the process comprises passing the gaseous feed stream to a feed side of a facilitated transport membrane comprising a polyethersulfone/polyethylene oxide-polysilsesquioxane blend support membrane, a hydrophilic polymer inside the pores on the skin layer surface of the support membrane, a thin, nonporous, hydrophilic polymer layer coated on the skin layer surface of the support membrane, and metal salts incorporated in the hydrophilic polymer layer coated on the skin layer surface of the support membrane and the the skin layer surface pores of the support membrane, wherein not less than 80 mole % of the olefins in the feed stream pass through the facilitated transport membrane to become a permeate stream and then recovering the permeate stream comprising not less than 90 mole % of olefin and not more than 10 mole % of paraffin or other gases such as nitrogen. An embodiment of the invention is one, any or all of prior embodiments in this paragraph up through the third embodiment in this paragraph wherein the polyethersulfone/polyethylene oxide-polysilsesquioxane blend support membrane comprises pores with an average pore diameter of less than 10 nm on the skin layer surface of the blend support membrane. An embodiment of the invention is one, any or all of prior embodiments in this paragraph up through the third embodiment in this paragraph wherein the blend support membrane is an asymmetric integrally skinned membrane with either a flat sheet or hollow fiber geometry. An embodiment of the invention is one, any or all of prior embodiments in this paragraph up through the third embodiment in this paragraph wherein the hydrophilic polymer inside the pores on the skin layer surface of the polyethersulfone/polyethylene oxide-polysilsesquioxane blend support membrane is selected from the group consisting of chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof. An embodiment of the invention is one, any or all of prior embodiments in this paragraph up through the third embodiment in this paragraph wherein the hydrophilic polymer in the thin, nonporous, hydrophilic polymer layer coated on the skin layer surface of the polyethersulfone/polyethylene oxide-polysilsesquioxane support membrane and the hydrophilic polymer inside the pores on the skin layer surface of the polyethersulfone/polyethylene oxide-polysilsesquioxane blend support membrane is selected from the same hydrophilic polymer or different hydrophilic polymers. An embodiment of the invention is one, any or all of prior embodiments in this paragraph up through the third embodiment in this paragraph wherein the hydrophilic polymer in the thin, nonporous, hydrophilic polymer layer coated on the skin layer surface of the polyethersulfone/polyethylene oxide-polysilsesquioxane blend support membrane is chitosan and the hydrophilic polymer inside the pores on the skin layer surface of the polyethersulfone/polyethylene oxide-polysilsesquioxane blend support membrane is sodium alginate or sodium hyaluronate. An embodiment of the invention is one, any or all of prior embodiments in this paragraph up through the third embodiment in this paragraph wherein the metal salts are selected from the group consisting of silver salts and copper salts.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A membrane comprising a polyethersulfone/polyethylene oxide-polysilsesquioxane blend support membrane comprising a polyethylene oxide-polysilsesquioxane polymer and a polyethersulfone polymer, wherein said polyethersulfone/polyethylene oxide-polysilsesquioxane blend support membrane is an asymmetric integrally skinned membrane; a hydrophilic polymer inside the pores on the skin layer surface of the polyethersulfone/polyethylene oxide-polysilsesquioxane blend support membrane; a hydrophilic polymer coated on the skin layer surface of the polyethersulfone/polyethylene oxide-polysilsesquioxane blend support membrane, and metal salts incorporated in the hydrophilic polymer coating layer and the the skin layer surface pores of the polyethersulfone/polyethylene oxide-polysilsesquioxane blend support membrane.

2. The membrane of claim 1 wherein said polyethersulfone/polyethylene oxide-polysilsesquioxane blend support membrane comprises pores with an average pore diameter of less than 10 nm on the skin layer surface of said blend support membrane.

3. The membrane of claim 1 wherein said asymmetric integrally skinned membrane has either a flat sheet or hollow fiber geometry.

4. The membrane of claim 1 wherein said hydrophilic polymer inside the pores on the skin layer surface of the polyethersulfone/polyethylene oxide-polysilsesquioxane blend support membrane is selected from the group consisting of chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof.

5. The membrane of claim 1 wherein the hydrophilic polymer in the thin, nonporous, hydrophilic polymer layer coated on the skin layer surface of the polyethersulfone/polyethylene oxide-polysilsesquioxane support membrane and the hydrophilic polymer inside the pores on the skin layer surface of the polyethersulfone/polyethylene oxide-polysilsesquioxane blend support membrane is selected from the same hydrophilic polymer or different hydrophilic polymers.

6. The membrane of claim 5 wherein the hydrophilic polymer in the thin, nonporous, hydrophilic polymer layer coated on the skin layer surface of the polyethersulfone/polyethylene oxide-polysilsesquioxane blend support membrane is chitosan and the hydrophilic polymer inside the pores on the skin layer surface of the polyethersulfone/polyethylene oxide-polysilsesquioxane blend support membrane is sodium alginate or sodium hyaluronate.

7. The membrane of claim 1 wherein the metal salts are selected from the group consisting of silver salts and copper salts.

8. A method of making a facilitated transport membrane comprising:
(a) preparing a polyethersulfone/polyethylene oxide-polysilsesquioxane blend support membrane using a homogeneous solution comprising polyethersulfone, N,N'-bis-[(3-triethoxysilylpropyl)aminocarbonyl]-polyethylene oxide monomer, a mixture of a solvent, one or more non-solvents, and additives, wherein said polyethersulfone/polyethylene oxide-polysilsesquioxane blend support membrane is an asymmetric integrally skinned membrane;
(b) incorporating a hydrophilic polymer inside pores on the skin layer surface of said polyethersulfone/polyethylene oxide-polysilsesquioxane blend support membrane;
(c) coating a thin, nonporous, hydrophilic polymer layer on the skin layer surface of the polyethersulfone/polyethylene oxide-polysilsesquioxane blend support membrane; and
(d) impregnating the surface of the hydrophilic polymer-coated polyethersulfone/polyethylene oxide-polysilsesquioxane blend support membrane with an aqueous solution of a metal salt.

9. The method of claim 8 wherein said hydrophilic polymer is selected from the group consisting of chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof.

10. The process of claim 8 wherein said N,N'-bis-[(3-triethoxysilylpropyl)aminocarbonyl]-polyethylene oxide monomer hydrolyzes and polymerizes in the presence of a lactic acid catalyst to form said polyethylene oxide-polysilsesquioxane polymer.

11. A process to treat a gaseous feed stream comprising from 99 to 1 mole % of one or more C2-C8 olefins and from 1 to 99 mole % of one or more C1-C8 paraffins or other gases including nitrogen wherein said process comprises passing the gaseous feed stream to a feed side of a facilitated transport membrane comprising a polyethersulfone/polyethylene oxide-polysilsesquioxane blend support membrane, wherein said polyethersulfone/polyethylene oxide-polysilsesquioxane blend support membrane is an asymmetric integrally skinned membrane, a hydrophilic polymer inside the pores on the skin layer surface of said support membrane, a thin, nonporous, hydrophilic polymer layer coated on the skin layer surface of said support membrane, and metal salts incorporated in said hydrophilic polymer layer coated on the skin layer surface of said support membrane and the the skin layer surface pores of said support membrane, wherein not less than 80 mole % of the olefins in said feed stream pass through said facilitated transport membrane to become a permeate stream and then recovering the permeate stream comprising not less than 90 mole % of olefin and not more than 10 mole % of paraffin or other gases including nitrogen.

12. The process of claim 11 wherein said polyethersulfone/polyethylene oxide-polysilsesquioxane blend support membrane comprises pores with an average pore diameter of less than 10 nm on the skin layer surface of said blend support membrane.

13. The process of claim 11 wherein said asymmetric integrally skinned membrane has either a flat sheet or hollow fiber geometry.

14. The process of claim 11 wherein said hydrophilic polymer inside the pores on the skin layer surface of the polyethersulfone/polyethylene oxide-polysilsesquioxane blend support membrane is selected from the group consisting of chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof.

15. The process of claim 11 wherein the hydrophilic polymer in the thin, nonporous, hydrophilic polymer layer coated on the skin layer surface of the polyethersulfone/polyethylene oxide-polysilsesquioxane support membrane and the hydrophilic polymer inside the pores on the skin layer surface of the polyethersulfone/polyethylene oxide-polysilsesquioxane blend support membrane is selected from the same hydrophilic polymer or different hydrophilic polymers.

16. The process of claim 15 wherein the hydrophilic polymer in the thin, nonporous, hydrophilic polymer layer coated on the skin layer surface of the polyethersulfone/polyethylene oxide-polysilsesquioxane blend support membrane is chitosan and the hydrophilic polymer inside the pores on the skin layer surface of the polyethersulfone/polyethylene oxide-polysilsesquioxane blend support membrane is sodium alginate or sodium hyaluronate.

17. The process of claim 15 wherein the metal salts are selected from the group consisting of silver salts and copper salts.

* * * * *